Aug. 1, 1972 R. S. MOORE Plant Pat. 3,246
MINIATURE ROSE PLANT
Filed Jan. 11, 1971
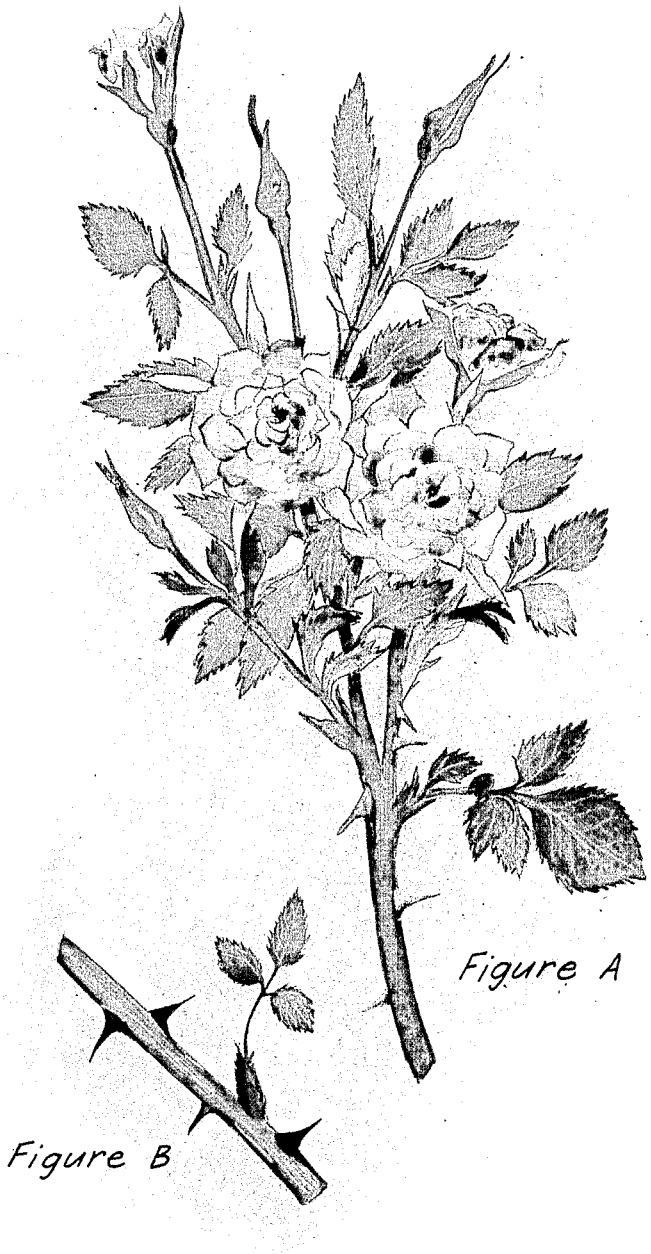
WITNESS
Jeanette Nunn Copley
INVENTOR
Ralph S. Moore United States Patent Office Plant Pat. 3,246

Patented Aug. 1, 1972

3,246

MINIATURE ROSE PLANT

Ralph S. Moore, 2519 E. Noble Ave.,
Visalia, Calif. 93277

Filed Jan. 11, 1971, Ser. No. 105,745
Int. Cl. A01h 5/00
U.S. Cl. Plt.—10 1 Claim The present invention relates to a new and distinct variety of hardy, dwarf, bush type rose plant of the miniature class; the variety being primarily characterized—as to novelty—by bright red buds and flowers which in general color effect are a glowing red similar in color to "Scarlet Gem" (Miniature—Pat. No. 2155), and which tend to become darker red as the flower matures.

The variety is further characterized by:

An abundance of bloom, with flowers borne singly or several to the stem in loose clusters.
Sweet fragrance.

A plant which is vigorous, of rounded spreading shape and with semi-glossy, moderately small foliage with pointed leaflets; the buds and flowers being similar in form and size to the variety "Tiny Jack" (United States Plant Pat. No. 2484). The plant, which has a normal height of 10 to 12 inches can easily be maintained at 8 inches or less by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, California, under conditions of careful control and observation, as a cross between "Little Darling" (Floribunda—Plant Pat. No. 1581, expired) as the seed parent and "Magic Wand" (Miniature—not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf; bush; seedling; greenhouse; outdoors; cut flowers; garden decoration; potted plant.
Class: Miniature.
Flowers: Continuity; continuous—repeat bloom all season. Fragrance; moderate, sweet.
Flowers borne: Singly and several together (3 to 5) on strong, medium length stems.
Quantity of bloom: Abundant both outside and in greenhouse.
Bud:

*Peduncle.*—Medium length; slender but sturdy; erect; medium green, sometimes tinted bronze; hairs—few to none. Before calyx breaks; size—small. Form medium long; pointed; with a few foliaceous appendages and numerous tiny short hairs on surface of bud; with foliaceous parts extending beyond the tip of the bud equal to one half or more of its length. Color—medium green, occasionally tinted with bronze. As calyx breaks, color—medium to deep red. As first petal opens: same color but showing yellow tones near base of petal; size small.

Bloom:

*Size when fully open.*—small, averaging about 1¼ inch.

*Petalage.*—double-40 (plus several narrow petaloids) arranged regularly.

*Form.*—slightly cupped at first, becoming more rounded in the center, with petals rolled loosely outward, and later a maturity rounded with higher center with petals rolled loosely outward and downward. Edges of petals tend to fold back imparting a pointed effect.

Petals: Fairly thick; satiny both inside and outside.

*Shape.*—Outside petals, broad lanceolate (almost round with pointed base); Intermediate: broad lanceolate with rounded tip; Inside—lanceolate with acute tip.

Newly opened flower from a plant grown outdoors (October 1970), Visalia, California.

*Color: Outside petal.*—Outside surface—Crimson 22 (often with darker shading) blending into cream, yellow and greenish tints at base; Inside surface—Crimson 22 (sometimes with darker shading) blending into cream and yellow at base. Intermediate petal—Outside surface—Crimson 22/1 or darker, blending into bright yellow at base; inside surface—Crimson 22 with darker shadings, blending into bright yellow at base. Inner petal—Outside surface—same as intermediate petal; Inside surface—same as intermediate petal. General color effect newly opened flowers—bright red color, similar to "Scarlet Gem". Three days open—darker red color.

*Behavior.*—As flowers age petals may become darker shade before dropping off. Spent petals drop off. Flower color is often lighter medium red shade when grown in greenhouse. Flower longevity (October 1970)—bush in garden or pot 4 to 5 days or longer. Cut flowers at living room temperature, 4 to 6 days.

*Reproductive organs*

Stamens: Few to average, arranged irregularly about pistil; sometimes mixed with petaloids.
Filaments: Short; yellow.
Pollen: Small amount; yellow.
Pistils: Average number.
Styles: Uneven; short; bunched; color—red.
Stigma: Nearly white or pale yellow.
Ovaries: All enclosed in calyx.
Hips: None.
Sepals: Permanent; spear shaped; lightly recurved.
Seeds: None.
Foliage:

*Leaves.*—Compound of five leaflets, sometimes seven; abundant; small to moderately small; leathery, semiglossy.

*Leaflets.*—Shape—Lanceolate; apex acute; base acute or rounded acute. Margin serrate. Color.—Normal green; new growth—reddish or tinted bronze. Rachis.—Medium strength; upper side smooth, grooved; under side sparsely thorny with few very tiny prickles. Stipules.—Fairly long; medium width; medium length narrow points which may turn out at both more or less than 45 degrees Growth:

*Habit.*—Dwarf; bushy; rounded; much branched.

*Growth.*—Free; vigorous.

*Canes.*—Medium; slender.

*Main stems.*—Color—dull green. Thorns—few; medium length; hooked slightly downward; Color— brown or reddish-brown. Prickles—none. Hairs—none.

*Branches.*—Color—medium green. Thorns—sparsley thorny. Medium length; very slender; nearly straight; medium to short oval base. Prickles—none. Hairs—none.

*New shoots.*—Color—usually tinted red or bronze. Thorns—few to moderate (often none); medium length; straight, reddish color; sharp points; base oval. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

1. A new and distinct variety of miniature rose plant of hardy, dwarf, rounded, much branched, bush type, as illustrated and described, characterized by buds and flowers resembling the "Tiny Jack" (Plant Pat. No. 2484) miniature rose in general form, the color being a brighter shade of red; the general color effect being bright red—of a shade resembling "Scarlet Gem" (Miniature, Plant Pat. No. 2155); and further characterized by a plant which is of vigorous and compact growth habit but more dwarf than "Tiny Jack", easy to propagate from cuttings; with small semi-glossy foliage, tinted reddish or bronze on new growth; with flowers borne singly or several to stem in loose clusters.

No references cited.

ROBERT E. BAGWILL, Primary Examiner